United States Patent
Stelzle et al.

(10) Patent No.: US 7,481,912 B2
(45) Date of Patent: Jan. 27, 2009

(54) PAIR OF MEASURING ELECTRODES, BIOSENSOR COMPRISING A PAIR OF MEASURING ELECTRODES OF THIS TYPE, AND PRODUCTION PROCESS

(75) Inventors: Martin Stelzle, Reutlingen (DE); Wilfried Nisch, Tuebingen (DE)

(73) Assignee: NMI Naturwissenschaftliches und Medizinisches Institut an der Universität Tuebingen, Reutlingenm (DE)

( * ) Notice: Subject to any disclaimer, the term of this patent is extended or adjusted under 35 U.S.C. 154(b) by 803 days.

(21) Appl. No.: 10/688,771

(22) Filed: Oct. 16, 2003

(65) Prior Publication Data

US 2004/0134778 A1 Jul. 15, 2004

Related U.S. Application Data

(63) Continuation of application No. PCT/EP02/04222, filed on Apr. 16, 2002.

(30) Foreign Application Priority Data

Apr. 17, 2001 (DE) ................. 101 20 083

(51) Int. Cl.
*G01N 27/327* (2006.01)
*G01N 27/403* (2006.01)

(52) U.S. Cl. ............... 204/403.01; 977/957; 204/242

(58) Field of Classification Search ................. 204/403.01–403.15, 416–419, 242, 260, 204/272; 205/777.5, 778, 792, 775; 429/209
See application file for complete search history.

(56) References Cited

U.S. PATENT DOCUMENTS

| | | | |
|---|---|---|---|
| 5,187,096 A | * | 2/1993 | Giaever et al. ............ 435/287.1 |
| 5,204,239 A | * | 4/1993 | Gitler et al. ................... 435/7.1 |
| 5,328,847 A | * | 7/1994 | Case et al. .................... 205/778 |
| 5,882,496 A | * | 3/1999 | Northrup et al. ............. 204/601 |
| 6,004,450 A | * | 12/1999 | Northrup et al. ............. 205/656 |
| 6,705,152 B2 | * | 3/2004 | Routkevitch et al. ........ 73/31.05 |
| 6,946,197 B2 | * | 9/2005 | Yadav et al. ................. 428/402 |
| 7,144,486 B1 | * | 12/2006 | Fritsch et al. .......... 204/403.06 |

FOREIGN PATENT DOCUMENTS

WO   WO 00/62047   10/2000

OTHER PUBLICATIONS

U.S. Appl. No. 60/242,905, filed Oct. 24, 2000.*
Musil, et al., Nanostructuring of Gold Electrodes for Immunosensing Applications, *Journal of Vacuum Science and Technology*, American Institute of Physics, New York, NY; Bd. 13, No. 6; Nov./Dec. 1995; pp. 2781-2786.

(Continued)

*Primary Examiner*—Alex Noguerola
(74) *Attorney, Agent, or Firm*—Knobbe Martens Olson & Bear LLP

(57) ABSTRACT

A pair of measuring electrodes comprising a first and a second, preferably in each case sheet-like electrode comprises an insulation layer arranged between said electrodes. One or more nanopores, which extend through said insulation layer as far as said first electrode, the surface of which is at least partially uncovered by said nanopores, are provided in each second electrode. The invention also describes a biosensor comprising a pair of measuring electrodes of this type, an electrochemical cell comprising a biosensor of this type and a process for producing said pair of measuring electrodes.

10 Claims, 2 Drawing Sheets

OTHER PUBLICATIONS

Nagale, et al., Individually Addressable, Submicrometer Band Electrode Arrays. 1. Fabrication From Multilayered Materials, *Analytical Chemistry*, American Chemical Society, Columbus, US; Bd. 70, No. 14, Jul. 15, 1998; pp. 2902-2907.

Niwa, et al., Highly Sensitive and Selective Voltammetric Detection of Dopamine With Vertically Separated Interdigitated Array Electrodes, *Electroanalysis*, VHC Publishers, Inc., U.S.; Bd. 3; 1991; pp. 163-168.

* cited by examiner

PAIR OF MEASURING ELECTRODES, BIOSENSOR COMPRISING A PAIR OF MEASURING ELECTRODES OF THIS TYPE, AND PRODUCTION PROCESS

CROSS-REFERENCES TO RELATED APPLICATIONS

This application is a continuation of copending International Patent Application PCT/EP02/04222 filed on Apr. 16, 2002, and designating the US, which was not published under PCT Article 21(2) in English, and claims priority of German Patent Application DE 101 20 083.8, filed on Apr. 17, 2001, which is incorporated herein by reference.

BACKGROUND OF THE INVENTION

1. Field of the Invention

The present invention relates to a pair of measuring electrodes, to a biosensor comprising at least one pair of measuring electrodes of this type, to an electrochemical cell comprising a biosensor of this type and to a process for producing the pair of measuring electrodes.

2. Related Prior Art

Numerous pairs of measuring electrodes and biosensors of this type are known from the prior art; cf. for example WO 99/07879, WO 00/62047 or WO 00/62048, as well as the very wide range of possible applications and uses described therein.

The biosensors described in these documents have arrays of pairs of measuring electrodes which can be addressed individually and each of which pairs has two electrodes which are arranged parallel to one another in one plane and may be designed as fingers entangled into one another, so-called interdigitated electrodes, or as interleaved, concentric sections of a circle.

The known biosensors are used, for example, to determine concentrations of biomolecules, to determine physico-chemical properties, to detect immune reactions and the like. In general terms, biosensors of this type are used in analytical or immunological assays, where they are used as amperometric sensors to measure extremely low concentrations. However, the measuring electrodes can also be used for electrostimulation, for electrophoretic enrichment or separation of charged molecules or, for example, for electrochemical recording of reaction sequences.

The amperometric sensors mentioned detect currents which emanate from oxidation or reduction reactions at molecules in solution in the vicinity of the electrodes. A selectivity for a specific molecule species can be achieved because certain redox-active molecules are reduced or oxidized at a specific potential. The current measured is proportional to the concentration of the molecules in the solution.

Depending on the type of reaction involved, the transferred charge per molecule is one or a few elemental charges, whereby it is possible to increase the sensitivity by what is known as redox recycling. For this purpose, the electrodes are arranged at a very short distance from one another, so that a redox-active molecule can diffuse to and fro between the anode for the oxidation reaction and the cathode for the reduction reaction with a high probability. In the process, the molecule takes up charge a number of times at the cathode (reduction) and releases it again at the other electrode, the anode (oxidation); cf. Niwa et al., Electroanalysis 3 (1991), 163-168.

To enable the redox recycling phenomenon to be exploited, the dimensions of and distance between the electrodes must be as small as possible in order to allow a rapid diffusion of the molecules between anode and cathode. Niwa et al., loc. cit., in this context describe two different electrode arrangements, in which the distances between anode and cathode and the widths of anode and cathode are as little as 1 µm and the length is 2 mm. In one embodiment, up to 100 interdigitated fingers lie next to one another in one plane, while in the other embodiment anode and cathode fingers are vertically spaced apart by an insulation, resulting in a regularly structured array having microstrips. The electrodes are produced by conventional photolithography and etching techniques.

In order to achieve the selectivity, which is not sufficient in the case of the vertical arrangement, the authors propose a further reduction in the dimensions or the use of selected polymers.

SUMMARY OF THE INVENTION

Against this background, one object underlying the present invention is to provide a pair of measuring electrodes of the type mentioned at the outset which has a very high sensitivity and is simple and inexpensive to produce.

According to the invention, this object is achieved by a pair of measuring electrodes comprising a first and a second, preferably in each case planar or sheet-like electrode and an insulation layer arranged between the electrodes, in which pair one or more nanopores are provided in the second electrode, extending through the insulation layer to the first electrode, the surface of which is at least partially uncovered in the nanopores.

The object underlying the invention is thereby completely achieved.

This is because the inventor of the present application has recognized that it is possible to build up the pairs of measuring electrodes from in each case two, preferably sheet-like electrodes which are arranged parallel and are spaced apart from one another by an insulation layer, and to provide nanopores in the upper electrode, which nanopores extend through the insulation layer down to the lower electrode, which lower electrode is therefore partially exposed in the nanopores. In the context of the present invention, the term "nanopores" is understood as meaning openings or recesses which in cross section are not necessarily circular or of any other regular shape and which have an opening width that is submicron. The width may be, for example, from approximately 20 to 500 nm. In one embodiment it may be approx. 100 nm. In certain embodiments, the depth of the nanopores is substantially determined by the thickness of the insulation layer, which amounts to approximately 10 to 200 nm. In one embodiment, the thickness of the insulation layer may be approx. 50 nm.

The nanopores do not have to be arranged regularly, but rather they may be arranged irregularly or randomly regularly. The number of nanopores per unit area, i.e. their density, may vary within a wide range, provided that it is ensured that the perforated upper electrode still remains conductive in the lateral direction and that adjacent nanopores are separated from one another by remaining material of the insulation layer.

The inventor has realized that, by turning away from the standard finger electrodes, it is possible to create pairs of measuring electrodes, in particular for biosensors, which have a very high sensitivity and selectivity, since not only the distance between the electrodes can be reduced virtually to any desired degree, but also the large number of nanopores which is possible per pair of measuring electrodes also means that an extremely high number of molecules contributes to the measurement current in the redox recycling process. On account of the small diameter of the nanopores and the small thickness of the insulation layer, there are also very short diffusion paths, meaning that the molecules can take up charge and release it again very frequently per unit time, which likewise contributes to increasing the sensitivity.

In this context, it is preferred if the electrodes have a diameter of approx. 1 µm to approx. 10 mm, preferably of approx. 10 µm, the pair of measuring electrodes preferably being applied to an insulating substrate which further preferably comprises glass, silicon/silicon oxide or a polymer. The electrodes may in this case contain metal, preferably gold, platinum, palladium, iridium or carbon or a carbon compound, the insulation layer preferably comprising a silicon compound or a polymer layer.

In one embodiment, it is preferred if the nanopores make up at least approx. 5%, preferably more than 60%, of the surface area of the first electrode.

In a further configuration of the pair of measuring electrodes according to the invention, only one or a few nanopores are provided per pair of measuring electrodes. This configuration relates to an application in which redox processes at individual molecules are to be detected by measuring fluctuations in the current signal in order to obtain information as to the diffusion and kinetics of the redox process. For this purpose, it is necessary that only one or a very small number of nanopores contributing to the overall current are lying in the electrode structure, which in terms of its external dimensions and in view of the cost aspect, may still be on a micrometer scale. In this configuration, the amplitude of fluctuations relative to the mean of the measurement current then becomes so great that it can be measured. Therefore, for certain applications it is preferred and advantageous if only one or a small number of nanopores are present in the pair of measuring electrodes. The number of nanopores can easily be set during the production process, which is described in more detail below.

In this configuration, it is possible to use the novel pair of measuring electrodes to measure current fluctuations in order to clarify diffusion and kinetics of redox molecules.

Another object of the present invention relates to a biosensor at least comprising one pair of measuring electrodes of this type, and to an electrochemical cell comprising a biosensor of this type.

The biosensor may include a multiplicity of the novel pairs of measuring electrodes, which can all be read out by dedicated supply lines. The pairs of measuring electrodes are preferably interrogated or read-out via a potentiostat circuit, the reference electrode and counterelectrode of which may be arranged either in an electrochemical cell in which the biosensor is located and to which an electrolyte containing molecules to be measured is added, or on the biosensor itself.

In general terms, it is preferred if at least one further electrode, which serves as a reference electrode or counterelectrode and preferably has a surface area which is greater, preferably at least 10 times greater, than the surface area of the second electrode, is provided on the substrate in the biosensor. In one embodiment, the biosensor is designed as a chip with supply conductors for the electrodes.

In one embodiment, the electrochemical cell has a receiving space for an electrolyte in which molecules which are to be recorded using the biosensor are present, the electrochemical cell preferably having terminals for a readout circuit, preferably a potentiostat circuit.

The specificity for redox molecules which are to be analyzed can be set by coating the pores and/or electrodes. In this case, it is possible to use monolayers, polymer layers, in particular polyelectrolyte layers and hydrogels. The electropolymerization process is particularly preferred in this context, since localization of the coating specifically on the electrodes and in the nanopores can be induced automatically by the application of current. The nanopores can in this case be coated with an ion-selective membrane or with a membrane with embedded enzymes. For a sensor application, it is also possible to provide a coating with polymer and an embedding of redox-active molecules by electropolymerization.

The novel pair of measuring electrodes can also be used as a microsensor for microelectrode arrangements in order to detect neurotransmitters and nitrogen oxides (NO). The production of the pairs of measuring electrodes can be easily integrated in the process for producing microelectrode arrangements. This results in the advantage of high sensitivity on account of the nanopores, also exploiting the advantage that a physiological signal can be measured in the form of the concentration of chemical substances.

The novel pairs of measuring electrodes can in principle be produced in various ways. It is possible to use the following process, which likewise is an object of the invention:

a) applying a first, preferably sheet-like electrode to an insulating substrate, the electrode preferably having a layer thickness of approx. 50 to approx. 1000 nm, particularly preferably of approx. 100 to 200 nm, b) applying an insulation layer to the first electrode, c) masking the insulation layer using a nanostructured shadow mask made from nanoparticles which preferably have a diameter of 20 to 1000 nm, particularly preferably of approx. 100 nm, d) applying a second electrode to the insulation layer, without any electrode material being deposited in the region of the nanoparticles, the electrode having a layer thickness in the region of the radius of the nanoparticles, preferably a layer thickness of approx. 20 to approx. 500 nm, particularly preferably of approx. 50 nm, e) removing the nanoparticles, and f) etching the insulation layer up to the first electrode, with the second electrode serving as an etching mask.

An advantage of this process is that there is no need for photolithography or electron beam lithography to be used to structure the nanopores, and the process is very simple and inexpensive to carry out. The novel process makes it possible to produce extremely small inter-electrode distances in a simple way and to achieve a correspondingly high efficiency of the redox recycling, i.e. a high sensitivity.

In the novel process, therefore, first of all a first, sheet-like electrode is applied to a substrate, and then an insulation layer is applied to the first electrode. Conventional photolithography can be used to microstructure the contours of the first electrode. Then, a structured shadow mask made from nanoparticles is deposited on the insulation layer before the second, sheet-like electrode is applied. After the nanoparticles have been removed, a nanostructured upper electrode remains, which is then used as an etching mask in order to etch the insulation layer selectively in the region of the openings in the upper electrode. The etching process stops at the lower electrode, so that nanopores are formed, in which the lower electrode is partially exposed.

The nanoparticles are preferably deposited from a solution where they are deposited regularly, in a random distribution, by means of a self-organization process.

The density of the nanoparticles acting as shadow masks on the insulation layer can be set by means of the concentration of nanoparticles in the solution. This is because on the one hand it may be advantageous for sensor applications to produce a density of nanopores as high as possible in order to achieve a high current density. On the other hand, to observe redox processes at individual molecules, it may be advantageous to produce a sensor electrode having only one or a small number of nanopores.

A process for producing nanostructured electrodes for measurements at immobilized biomolecules is known from the publications by Musil et al., J. Vac. Sci. Technol. 13 (1995), 2781-2786, and also Padeste et al., J. Electrochem. Soc. 143 (1996), 3890-3895.

In the known process, gold electrodes are deposited on an insulating substrate which, as shadow mask, includes randomly distributed nanoparticles. After the nanoparticles have been removed, what remains is a gold electrode with irregularly arranged holes in which the substrate is uncovered. Analyte molecules, such as for example antibodies, are immobilized on the substrate in the holes and can in this way be arranged very close to the readout electrode. Neither publication deals with pairs of measuring electrodes or with redox recycling.

To produce the novel pair of measuring electrodes, it is also possible to employ the following process, which also is an object of the invention:

a) applying a first, preferably sheet-like electrode to an insulating substrate, the electrode preferably having a layer thickness of approx. 50 to approx. 1000 nm, particularly preferably of approx. 100 to 200 nm, b) masking the first electrode using a nanostructured shadow mask made from nanoparticles, which preferably have a diameter of 10 to 1000 nm, particularly preferably of approx. 100 nm, c) applying an insulation layer to the first electrode, without any insulation material being deposited in the region of the nanoparticles, d) applying a second electrode to the insulation layer, without any electrode material being deposited in the region of the nanoparticles, the electrode having a layer thickness in the region of the radius of the nanoparticles, preferably a layer thickness of approx. 20 to approx. 500 nm, particularly preferably of approx. 50 nm, and e) removing the nanoparticles.

As an alternative to the above-described applying of the nanoparticles to the insulation layer as shadow mask for the electrode deposition, in this case the nanoparticles have already been applied to the first electrode. Then, insulation layer and second electrode are deposited and the nanoparticles are dissolved again. As a result, the insulation layer and the second electrode are structured directly, and the nanopores have then been completed, eliminating the etching process from step f) of the other process.

The nanostructured shadow mask used may either be nanoparticles deposited from a solution or alternatively a shadow mask produced by microtechnology, i.e. a grid with nanopores through which vapor deposition or sputtering is carried out, in which case subsequent inversion of the structure of islands produced in this way can be effected by known thin-film and micropatterning processes. The nanostructuring may also be carried out by applying a mask using a stamping process (nanoprinting) or by a forming process using a nanostructured stamp (nanoimprinting).

The advantage in this case is that shadow mask or stamp only has to be produced once using high-resolution lithography methods, then afterwards can be used to manufacture a large number of sensors. Since it is only the size of the nanopores rather than their absolute position on the electrode which is important, there is no need for any particularly accurate alignment of the tool, making the production process correspondingly inexpensive.

According to another object, the production process comprises the steps of:

a) applying a first, preferably sheet-like electrode to an insulating substrate, the electrode preferably having a layer thickness of approx. 50 to approx. 1000 nm, particularly preferably of approx. 100 to 200 nm, b) applying an insulation layer to the first electrode, c) applying a nanostructured second electrode to the insulation layer, and d) etching the insulation layer as far as the first electrode, with the second electrode being used as an etching mask.

As an alternative to a nanostructured shadow mask for producing the second electrode or for use as an etching mask, it is also possible to produce a nanostructured second electrode by evaporation coating or sputtering or PECVD (plasma-enhanced chemical vapor deposition). If known low-melting materials, such as for example gold, tin, silver, indium, are used, at layer thicknesses of above approximately 5-10 nm a layer which does not yet effect complete coverage but is laterally conductive is produced. This process initially forms islands which grow together as the layer thickness increases. A layer of this type is laterally conductive within a certain layer thickness range, typically approx. 10 to 100 nm, but not completely continuous. A nanostructured layer of this type, like the layers produced with the aid of nanoparticles or nanostructured shadow masks, can be used both as an etching mask and as a second electrode. In this context, it is advantageous that there is no dedicated structuring step and there is no need to apply nanoparticles or other nanostructured shadow masks.

This production of a nanostructured shadow mask can take place in the following way:

Gold is vaporized in vacuo from a graphite crucible and is deposited on a suitable substrate. The coating rate is set at approximately 0.2-0.5 nm/s. The substrate used is, for example, a film of amorphous carbon, as is customary for layer analysis in transmission electron microscopy. The substrate temperature is 30° C. Under these conditions, first of all isolated nuclei are formed, and as the layer thickness increases these nuclei grow together, forming a laterally conductive but nanoporous layer.

The principles of nucleation and layer growth, which form the basis of this process, are extensively described in: Constantine A. Neugebauer: Condensation, Nucleation, and Growth of Thin Films, in: Handbook of Thin Film Technology, Leon I. Maissel and Reinhard Glang (eds), ch. 8, p. 32 ff. McGraw-Hill, 1970.

Advantageous configurations of the novel process and of the novel pair of measuring electrodes, of the biosensor and of the electrochemical cell are given in the dependent claims.

It will be understood that the abovementioned features can be used not only in the combination given but also on their own or in other combinations without departing from the scope of the present invention.

BRIEF DESCRIPTION OF THE DRAWINGS

Further advantages and features will emerge from the description and the appended drawing, in which.

DESCRIPTION OF PREFERRED EMBODIMENTS

Figure 1:
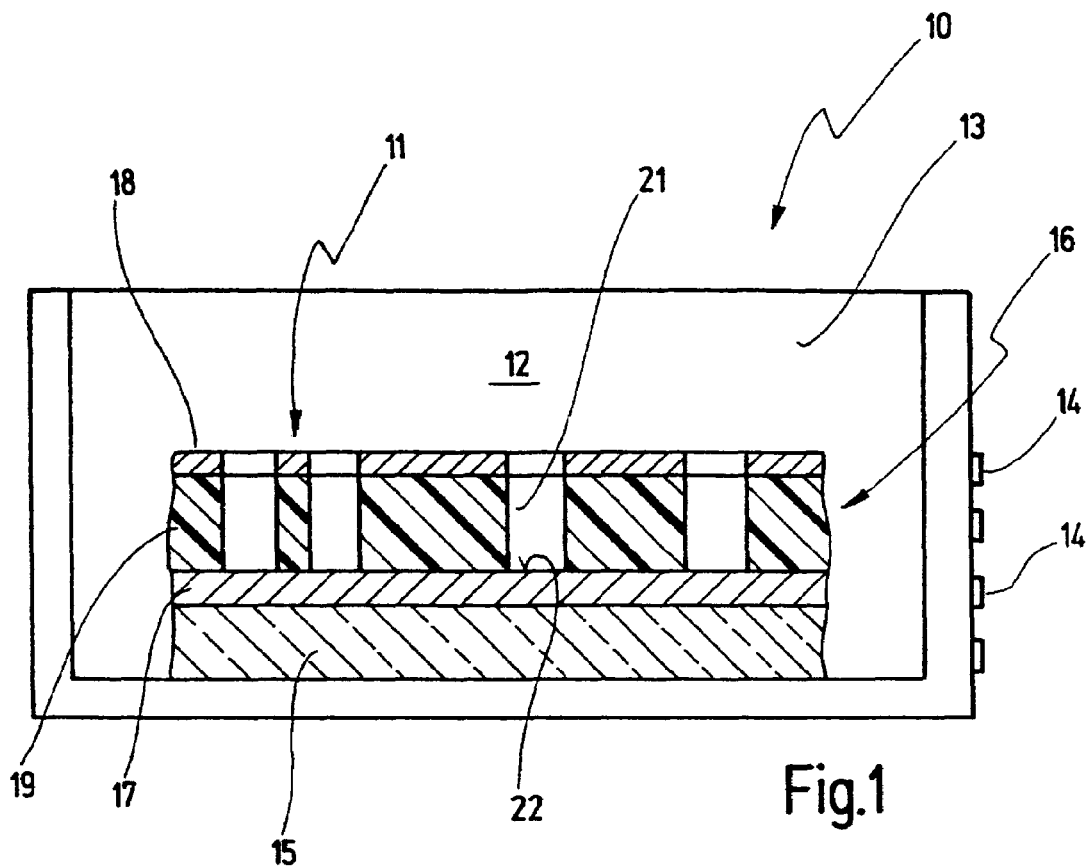
FIG. 1 shows an electrochemical cell in which a biosensor comprising a pair of measuring electrodes is illustrated in cross section and in excerpt form, not to scale, with exaggerated dimensions.

FIG. 1 shows a highly schematized, cross-sectional view of an electrochemical cell 10, in which a biosensor 11 is arranged which is used to measure molecules in an electrolyte located in a receiving space 13 of the cell 10. Terminals 14, which can be used for electrical connection of the biosensor 11, are arranged on the outside of the cell 10.

The biosensor 11, which is shown in an enlarged, not-to-scale form, comprises an insulating substrate 15 on which a pair 16 of measuring electrodes comprising a lower, first electrode 17 and an upper, second electrode 18 is arranged. Between the electrodes 17, 18 there is an insulation layer 19 which holds the electrodes spaced apart from one another. In the second electrode 18 and the insulation layer 19 there are nanopores 21 which extend as far as the surface 22 of the first electrode 17 which is uncovered in the nanopores 22. The nanopores are in a regular random distribution.

A process for producing a pair of measuring electrodes 17, 18 of this type comprises the following steps:

Applying a first, preferably sheet-like electrode 17 to an insulating substrate 15 made from glass, silicon/silicon oxide or a polymer layer, by sputtering or vapor deposition of gold, platinum, palladium, iridium or carbon, the electrode 17 preferably having a layer thickness of approx. 100 to 200 nm. In the case of carbon electrodes, a broader potential range is accessible than with metal electrodes, and consequently carbon electrodes are preferred for certain applications.

Applying an insulation layer 19 by sputtering or vapor deposition of silicon oxide or by spinning on a thin polymer film onto the first electrode 17. The layer thickness is preferably approx. 50 nm.

One further option for applying electrode and insulation layers is PECVD (plasma-enhanced chemical vapor deposition).

Next, the surface of the insulation layer 19 is pretreated in order to achieve a uniform distribution of nanoparticles on the surface. The pretreatment is dependent on the type of nanoparticles and the solvent in which they are brought to the surface. The surface may, for example, be made hydrophobic or hydrophilic, so that it can be wetted more successfully.

Masking the insulation layer 19 with a shadow mask made from nanoparticles which have a diameter of approx. 100 nm and are present in a solution (water, ethanol, toluene).

As an alternative to a shadow mask made from nanoparticles, it is also possible to use vapor-deposition particles, i.e. clusters, which form in a protective gas atmosphere, or a mask, which is produced by nanoprinting, nanoimprinting or vapor deposition or sputtering through a mask with nanopores produced by microtechnology.

Applying a second electrode 18 by sputtering or vapor deposition of metal on the insulation layer 19, without any electrode material being deposited in the region of the nanoparticles. The electrode 18 acquires a layer thickness which is in the region of the radius of the nanoparticles, preferably of approx. 50 nm.

Removing the nanoparticles, for which purpose the electrode 18 is exposed to ultrasound in a solvent, so that the nanoparticles (for example of latex) are removed from the surface.

Etching the insulation layer 19 as far as the first electrode 17, with the second electrode 18 serving as an etching mask. Wet-etching processes or dry-etching processes can be used for this purpose. In this way, the nanopores 21 in which the surface 22 of the first electrode 17 is uncovered are produced.

The processes of sputtering, vapor deposition and etching are known to the person skilled in the art, and in this context reference is made to the specialist literature. The masking of the insulation layer 19 may take place in the same way as described by Musil et al., loc. cit., or by Padeste et al., loc. cit.

Figure 2:
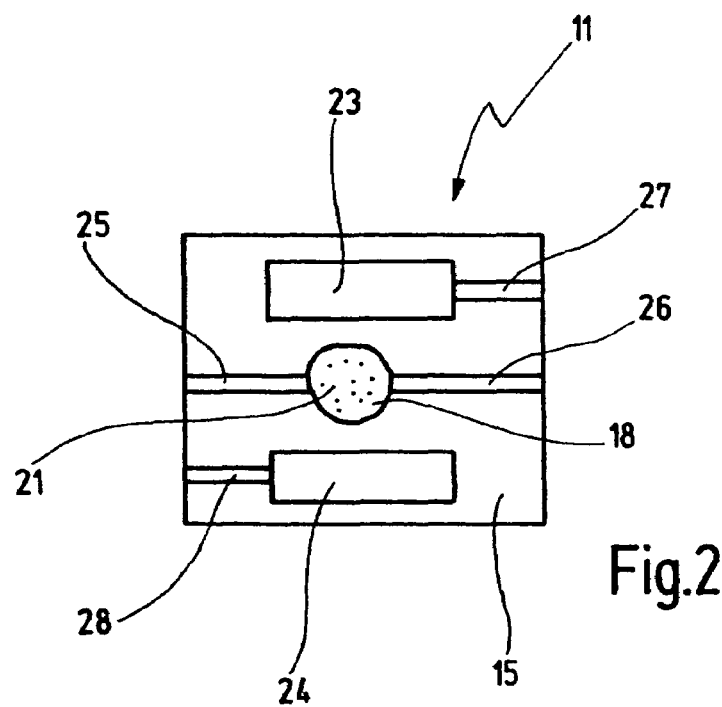
FIG. 2 shows a plan view of the biosensor from FIG. 1.

FIG. 2 shows the biosensor 11 from FIG. 1 in a plan view which is not to scale. It can be seen that further electrodes 23, 24, which serve as reference electrode and counterelectrode for a potentiostat circuit, are present on the substrate 15. The further electrodes 23, 24 have a surface area which is considerably larger than that of the second electrode 18. The nanopores 21 are in this case merely indicated as dots on the second electrode 18. Furthermore, on the substrate 15 supply lines 25, 26, 27 and 28 can be seen, which lead to the first electrode 17, the second electrode 18 and the further electrodes 23, 24, respectively. These supply lines are connected to the terminals 14 of the cell 10 shown in FIG. 1 when the biosensor 11 is inserted into the cell 10.

The pair 16 of measuring electrodes illustrated in FIGS. 1 and 2 can also be used to measure redox processes at individual molecules. In this case, only one or a small number of nanopores are produced in the second electrode 18 and in the insulation layer 19, while the contour dimensions of the electrodes 17 and 18, as in the embodiment with a large number of nanopores, may be in the micrometer range. On account of its external dimensions on the micrometer scale, the electrode structure can then still be produced at low cost, but on account of the fact that only one nanopore or a small number of nanopores is present, it is possible to detect measurements of fluctuations in the current signal in order to obtain information as to diffusion and kinetics of the redox process.

Figure 3:
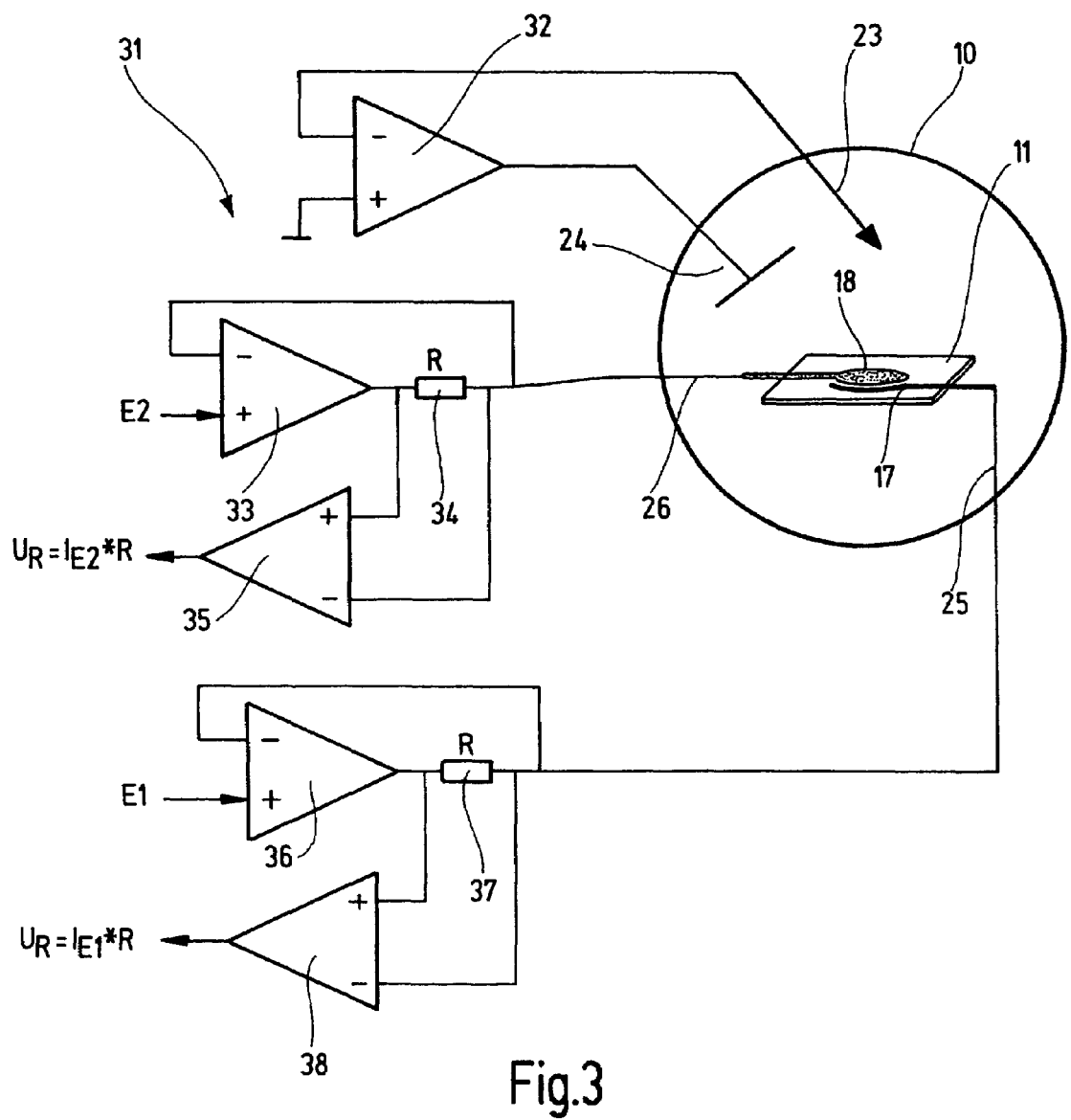
FIG. 3 shows a potentiostat circuit for reading out the electrochemical cell from FIG. 1.

FIG. 3 shows the cell 10 from FIG. 1 connected to a potentiostat circuit 31 for read-out of the biosensor 11. The reference electrode 23 and the counterelectrode 24 may also be provided in the cell 10 instead of on the biosensor 11. With regard to the function of the potentiostat circuit 31, reference is made to the corresponding literature which is accessible to the person skilled in the art.

The reference electrode 23 is connected to the inverting input of a potentiostat 32, the non-inverting input of which is at ground potential. The output of the potentiostat 32 is connected to the counterelectrode 24.

The supply line 26 leading to the second, upper electrode 18 of the biosensor 11 is connected to the output of a first differential amplifier 33 with negative feedback, with a series resistor 34 connected between them. Set potential E2 is applied to the non-inverting input of the differential amplifier 33, while the inverting input is connected to the supply line 26.

The voltage drop across the series resistor 34 is measured using a differential amplifier 35, the output of which therefore supplies a voltage signal which is proportional to the current flowing across the second electrode 18.

Correspondingly, the supply line 25 is connected to an output of a second differential amplifier 36 with negative feedback, likewise with a series resistor 37 connected between them. Set potential E1 is applied to the non-inverting input of the differential amplifier 36, while the inverting input is connected to the supply line 25 which leads to the first electrode 17 of the biosensor 11.

The voltage across the series resistor 37 is recorded using a differential amplifier 38, which at its output supplies a voltage signal which is proportional to the current flowing across the first electrode 17.

What is claimed is:

1. A bio sensor comprising:
   at least one pair of measuring electrodes, wherein the pair of measuring electrodes comprises a first and a second electrode and an insulation layer arranged between the electrodes, wherein one or more nanopores are provided in the second electrode, wherein the nanopores extend through the insulation layer to the first electrode, the surface of which is at least partially uncovered by the nanopores, and wherein the nanopores have an opening width selected from the range of approximately 20 nm to approximately 1000 nm, and wherein the at least one pair of measuring electrodes is arranged on a substrate; and
   at least one additional electrode arranged on the substrate, wherein the additional electrode serves as a reference electrode or counterelectrode.

2. The biosensor according to claim 1, wherein the additional electrode has a surface area which is greater than the surface area of the second electrode.

3. The biosensor according to claim 1, wherein the additional electrode has a surface area which is at least 10 times greater than the surface area of the second electrode.

4. The biosensor according to claim 1, wherein the biosensor is a chip with supply lines for the electrodes.

5. The pair of measuring electrodes according to claim 1, wherein the nanopores have an opening width of approximately 50 nm.

6. The pair of measuring electrodes according to claim 1, wherein the nanopores have an opening width of approximately 100 nm.

7. The pair of measuring electrodes according to claim 1, wherein the nanopores have an opening width of approximately 200 nm.

8. An electrochemical cell comprising:
   a biosensor, comprising:
      at least one pair of measuring electrodes, wherein the pair of measuring electrodes comprises a first and a second electrode and an insulation layer arranged between the electrodes, wherein one or more nanopores are provided in the second electrode, wherein the nanopores extend through the insulation layer to the first electrode, the surface of which is at least partially uncovered by the nanopores, and wherein the nanopores have an opening width selected from the range of approximately 20 nm to approximately 1000 nm, and wherein the at least one pair of measuring electrodes is arranged on a substrate; and
      at least one additional electrode arranged on the substrate, wherein the additional electrode serves as a reference electrode or counterelectrode; and
   a receiving space for an electrolyte, wherein the electrolyte comprises molecules to be recorded using the biosensor.

9. The electrochemical cell according to claim 8, wherein the cell comprises terminals for a readout circuit.

10. The electrochemical cell according to claim 9, wherein the readout circuit is a potentiostat circuit.

* * * * *